United States Patent
Shin (10) Patent No.: US 6,500,250 B1
(45) Date of Patent: Dec. 31, 2002

(54) COMPOUNDS FOR FORMING ALUMINA FILMS USING CHEMICAL VAPOR DEPOSITION METHOD AND PROCESS FOR PREPARING THE COMPOUND

(75) Inventor: Hyun-Koock Shin, Suwon (KR)

(73) Assignee: Rohn and Haas Company, Philadelphia, PA (US)

( * ) Notice: Subject to any disclaimer, the term of this patent is extended or adjusted under 35 U.S.C. 154(b) by 0 days.

(21) Appl. No.: 10/135,190

(22) Filed: Apr. 29, 2002

Related U.S. Application Data (63) Continuation of application No. 09/580,293, filed on May 26, 2000, now abandoned.

(51) Int. Cl.[7] .................. C07O 207/00; C07O 333/46; B05D 5/12
(52) U.S. Cl. .................. 106/287.17; 546/11; 548/402; 548/950; 548/969; 549/3
(58) Field of Search .................. 106/282.17; 546/11; 548/101, 402, 969; 549/3, 206, 208; 427/126.4, 255.19; 544/64, 225

(56) References Cited

U.S. PATENT DOCUMENTS

| | | |
|---|---|---|
| 4,923,717 A | 5/1990 | Gladfelter et al. |
| 5,178,911 A | 1/1993 | Gordon et al. |
| 5,180,687 A | 1/1993 | Mikoshiba et al. |
| 5,191,099 A | 3/1993 | Gladfelter et al. |
| 5,330,633 A | 7/1994 | Matsumoto et al. |
| 5,393,699 A | 2/1995 | Mikoshiba et al. |
| 5,900,279 A | 5/1999 | Hideaki et al. |

OTHER PUBLICATIONS

Atwood et al., "Mixed Donor and Monomeric N–Donor Adducts of Alane", *Inorg. Chem.* 32, pp 3482–3487, (1993). No Month Provided.

Wartik et al., "Reactions of Lithium Aluminum Hydride with Representative Elements of the Main Groups of the Periodic System", Contribution of the George Herbert Jones Laboratory of the University of Chicago, vol. 75, pp 835–839, (1952.) No month provided.

Thiele et al., "Electron donor–acceptor complexes of aluminum trialkyls with bivalent Lewis bases. II. Complexes of Trimethylaluminum with heterocyclic bidentate ligands" Z. Anorg. Allg. Chem. No. 3–4, (1996) No month provided pp. 179–188, pp. 187–188.

Sen et al., "Monomeric and dimeric complexes of Group IIIA Metal alkyls with piperidine. Effect of coordination on the carbon–metal bond", J. Inorg. Nucl. Chem., vol. 35, No. 7, (1973) No month provided pp. 2207–2215.

Beachley, O. T., Jr. et al. "Chelation in 1–5 organoaluminum–nitrogen chemistry" Inorg. Chem., vol. 15, No. 9, (1976) No month provided pp. 2110–2115, pp. 2111–2113.

Watkins et al., "27A1 and 13C NMR Relaxation Studies in Aminoalanese" Inorg. Chem., vol. 34, No. 24, (1995) No month provided pp. 6228–6230.

Styron, Eric KI. et al., "Reactivity of triethylaluminum with a series of secondary amines. Aduct and aminoalane dimer synthesis and characterization; the crystal structures of 'Et2A1N (c–CgH11) 2!2 and 'Et2A1NCH3!2", Polyhedron (1999) No month provided, 18(11), 1595–1602.

Henrickson et al., "Lewis acidity of alanes Interactions of trimethylalane with sulfides" Inorg Chem., vol. 6, No. 8, (1967) No month provided pp. 1461–1465.

Thomas, C. J. et al., "Reactivity of bis (trimethylaluminum) with selected aminoarsines and secondary amines" Polyhedron, vol. 12, No. 4, (1993) No month provided, pp. 389–399.

*Primary Examiner*—David Brunsman
(74) *Attorney, Agent, or Firm*—S. Matthew Cairns (57) ABSTRACT

Organometallic compounds useful for forming aluminum films by chemical vapor deposition are disclosed. Also disclosed are methods of preparing the organometallic compound and methods of forming aluminum films. The compounds are selected from R'R"R'"Al:$L_n$ wherein R', R", R'" are independently selected from alkyl, perfluroalkyl or alkoxy or borate. L is one or more organic Lewis bases selected from thiophene, thriopyran and,

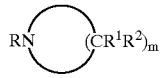

or

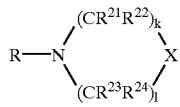

as defined in the instant specification.

10 Claims, 1 Drawing Sheet

Figure 1

COMPOUNDS FOR FORMING ALUMINA FILMS USING CHEMICAL VAPOR DEPOSITION METHOD AND PROCESS FOR PREPARING THE COMPOUND

This application is a continuation of copending application(s) application Ser. No. 09/580,293 filed on May 26, 2000, now abandoned.

BACKGROUND OF THE INVENTION

The present invention relates to precursor compounds useful for depositing alumina films used as a dielectric material in semiconductor devices, processes for preparing the compounds, and methods for vapor deposition of metallic films on silicon substrates using the compounds. More specifically, the present invention relates to compounds for forming alumina films upon adhesive layers or diffusion-preventive layers formed on substrates such as silicon substrates, processes for preparing the compounds, and methods for vapor deposition of metal oxide films.

According to the trend of large scale integration and miniaturization of semiconductor devices, the area occupied by memory cells, such as DRAM ("dynamic random access memory"), is rapidly decreasing. Therefore, it is important in the area of DRAM capacitors to guarantee sufficient capacitance within a small area.

Capacitance increases in proportion to the dielectric constant of a dielectric material and the area of dielectric film used in capacitor and is in inverse proportion to the thickness of film, and therefore, three possible approaches may be considered in order to obtain sufficient capacitance with the limited cell area of DRAM.

First, the cell structure of the capacitor may be converted into a 3-dimensional one in order to maximize the effective area of dielectric film within the restricted small area. Actually in the 4 mega-DRAM, the capacitor having a plane structure has been replaced with that having a stack or trench structure, each of which is a 3-dimensional one, for the purpose of enlarging the effective area. Also in the 16 mega- or 64 mega-DRAM, the effective area has been secured using the more complicated 3-dimensional capacitor such as a fin cylinder or crown.

However, this approach has the problem that very complex capacitor structures need to be formed in a cell having a small area. Therefore, adoption of such 3-dimensional structures in the manufacture of more than 256 mega-DRAM, such as 1 giga-DRAM, is restricted due to their increasing complexity and high cost.

Second, the thickness of the dielectric film may be decreased to guarantee the capacitance. However, even though the 3-dimensional capacitor structure is used for maximizing the effective area, if the existing NO ($Si_3N_4$/$SiO_x$) composite dielectric material is used, the thickness of dielectric film should be lowered to 40 to 45 Å in order for guaranteeing the minimum capacitance per cell, i.e. 25 to 30 fF (femptoFarad). Further, the reduction of thickness may result in the increase of current leakage due to the tunneling phenomenon or the increase of soft error by α-particles, and consequently, the reliability of device may be threatened seriously.

Third, another dielectric material having a higher dielectric constant may be used instead of the currently used one for capacitors, such as for example, ONO structure such as $SiO_2$/$Si_3N_4$/$SiO_x$ or NO structure such as $Si_3N_4$/$SiO_x$, having a lower dielectric constant. Under the situation as explained above, extensive studies have been carried out for forming dielectric films of a capacitor using materials having higher dielectric constants than the earlier developed ones, whereby the capacitance can be stably secured in the manufacture of the next generation memory of more than 256 mega-DRAM. Use of such films having high dielectric constants may settle the problems such as difficulties in manufacturing processes, complexity of capacitor structures, reduction of reliability of devices, etc. One of the dielectric films currently studied for that purpose is alumina film.

Since 1970s, the study of alumina CVD using commercially available alkyl aluminum and aluminum alkoxide was performed in the USA and Japan. The typical aluminum compounds used have been trimethylaluminum having the formula $Al(CH_3)_3$ and aluminum isopropoxide having the formula $Al(O-iC_3H_7)_3$.

The compounds as recommended above, however, show some problems when they are used as precursors. The alkylaluminum compound, trimethylaluminum, has been used for various purposes in different technical areas, and thus, it can be commercially purchased from the market with a low cost. Also, it has the advantage of being effectively used as the CVD precursor because it exists as a liquid having a high vapor pressure at room temperature. However, since the vapor deposition of film is achieved at a high temperature of 300 to 400° C., the undesirable impurity carbon may remain in the alumina film and a very careful handling may be required due to the explosive inflammation caused by the trifling contact of alkylaluminum compound with the ambient air, which commonly occurs when the alkyl aluminum compound is used.

The aluminum alkoxide compound, i.e., aluminum isopropoxide, is cheap and commercially available. Also, it does not inflame upon contact with moisture. However, it has the disadvantage that since it exists as a solid at room temperature or its vapor pressure is low, high temperature heating may be required at the stage of vapor deposition which results in the decomposition of the compound, or the deposition process may not be reproducible due to the condensation of the compound.

In the case of vapor-deposition of aluminum films using such compounds, several problems may occur, such as for example, the introduction of undesirable carbon impurities into the aluminum film; the difficult to achieve process reproducibility which is caused by the decomposition of precursor compound in the reactor due to the high temperature heating; and explosive inflammation caused by the reaction of the compound with moisture, etc.

SUMMARY OF THE INVENTION

In order to solve the problems mentioned above, the present inventor has complemented the earlier invention relating to a precursor compound for forming aluminum film via chemical vapor deposition method and process for preparing the same, which was filed by the present inventor as Korean Patent App. No. 98-38572, and as a result, completed the present invention.

The present invention provides a novel aluminum compound and process for preparing the same, by which can be solved some problems found in the prior art for precursor compounds for alumina and aluminum CVD, such as for example, difficult to achieve reproducibility of film deposition processes, explosive inflammation of the compounds upon contact with moisture, and the residual impurities in the film. Further, according to the present invention, the skilled person may enjoy the large range of selection of the precursor compounds.

In one aspect, the present invention provides an organometallic complex useful for depositing a highly pure alumina film on a substrate by chemical vapor deposition, having the Formula I:

wherein R', R" and R'" are independently selected from alkyl, perfluoroalkyl or alkoxy each of which has 1 to 5 carbon atoms, or borate ($BH_4$); L is one or more organic Lewis bases capable of providing an unshared electron pair to the aluminum metal center selected from thiophene, thiopyran and organic amines of the Formulae II or III:

wherein R is an alkyl having 1 to 4 carbon atoms; $R^1$, $R^2$, $R^{21}$, $R^{22}$, $R^{23}$ and $R^{24}$ are independently selected from hydrogen (H) or alkyl having 1 to 2 carbon atoms; X is oxygen (O) or nitrogen having alkyl group; k and l are integers of 1 to 3; m is an integer of 2 to 8; and n is an integer of 1 or 2.

In a second aspect, the present invention provides a vapor deposition precursor composition comprising an organometallic compound as described above and one or more heterocyclic amine solvents.

In a third aspect, the present invention provides a process for alumina film formation including the step of vapor depositing an alumina film on a substrate, wherein the source of aluminum in the alumina film is a vapor deposition precursor including an organometallic compound of the Formula:

wherein R', R" and R'" are independently selected from alkyl, perfluoroalkyl or alkoxy each of which has 1 to 5 carbon atoms, or borate ($BH_4$); L is one or more organic Lewis bases capable of providing an unshared electron pair to the aluminum metal center selected from thiophene, thiopyran and organic amines of the Formulae II or III:

wherein R is an alkyl having 1 to 4 carbon atoms; $R^1$, $R^2$, $R^{21}$, $R^{22}$, $R^{23}$ and $R^{24}$ are independently selected from hydrogen (H) or alkyl having 1 to 2 carbon atoms; X is oxygen (O) or nitrogen having alkyl group; k and l are integers of 1 to 3; m is an integer of 2 to 8; and n is an integer of 1 or 2.

In a fourth aspect, the present invention provides a process for preparing an organometallic compound of the Formula:

wherein R', R" and R'" are independently selected from alkyl, perfluoroalkyl or alkoxy each of which has 1 to 5 carbon atoms, or borate ($BH_4$); L is one or more organic Lewis bases capable of providing an unshared electron pair to the aluminum metal center selected from thiophene, thiopyran and organic amines of the Formulae II or III:

wherein R is an alkyl having 1 to 4 carbon atoms; $R^1$, $R^2$, $R^{21}$, $R^{22}$, $R^{23}$ and $R^{24}$ are independently selected from hydrogen (H) or alkyl having 1 to 2 carbon atoms; X is oxygen (O) or nitrogen having alkyl group; k and l are integers of 1 to 3; m is an integer of 2 to 8; and n is an integer of 1 or 2; including the step of combining in the absence of a solvent the organic Lewis base and a tri-substituted aluminum compound of the formula R'R"R'"Al, wherein R', R" and R'" are as defined above.

DETAILED DESCRIPTION OF INVENTION

The present invention relates to novel aluminum compounds useful as precursor compounds for metallic film deposition, as represented by the Formula 1, which are designed to retain the merits of the existing precursors for depositing an alumina film and as well to address the problems of such precursors.

Organic Lewis bases capable of providing an unshared electron pair to the aluminum center are useful in the present invention. Suitable organic Lewis bases include those of Formulae II and III. In particular, suitable Lewis bases include, but are not limited to, alkylaziridine, alkylazetidine, alkylpyrrolidine, alkylpiperidine, alkylhexamethyleneimine, alkylheptamethyleneirnine, alkylmorpholine, and 1,4-dialkylpiperazine.

In the above Formula II, R is an alkyl having 1 to 4 carbon atoms; $R^1$ and $R^2$ are independently selected from hydrogen (H) or alkyl having 1 to 2 carbon atoms; and m is an integer of 2 to 8.

In the above Formula III, R is as defined in Formula II; $R^{21}$, $R^{22}$, $R^{23}$ and $R^{24}$ are independently selected from hydrogen (H) or alkyl having 1 to 2 carbon atoms; X is selected from oxygen (O) or nitrogen having alkyl group; and k and l are integers of 1 to 3.

Among the compounds of Formula II, alkylaziridine (m=2 in Formula II) of the following Formula IV, alkylpyrrolidine (m=4 in Formula II) of the following Formula V and alkylpiperidine (m=5 in Formula II) of the following Formula VI are preferred. Among the compounds of Formula III, alkylmorpholine of the following Formula VII and alkylpiperazine of the following Formula VIII are preferred, and compounds of Formula VIII are more preferred.

(IV)

(V)

(VI)

In the above Formula IV, R is an alkyl having 1 to 4 carbon atoms; and $R^2$ is selected from hydrogen or alkyl having 1 to 2 carbon atoms. Suitable compounds of Formula IV include those wherein R is methyl or ethyl and $R^2$ is hydrogen or methyl. In the compounds of Formula V, R is an alkyl having 1 to 4 carbon atoms; $R^3$, $R^4$, $R^5$, $R^6$, $R^7$, $R^8$, $R^9$ and $R^{10}$ are independently selected from hydrogen or alkyl having 1 to 2 carbon atoms. In the compounds of Formula VI, R is an alkyl having 1 to 4 carbon atoms; and $R^{11}$, $R^{12}$, $R^{13}$, $R^{14}$, $R^{15}$, $R^{16}$, $R^{17}$, $R^{18}$, $R^{19}$ and $R^{20}$ are independently selected from hydrogen or alkyl having 1 to 2 carbon atoms.

(VII)

(VIII)

In the above formula 7, R is an alkyl having 1 to 4 carbon atoms; and $R^{25}$, $R^{26}$, $R^{27}$, $R^{28}$, $R^{29}$, $R^{30}$, $R^{31}$, and $R^{32}$ are independently selected from hydrogen or alkyl having 1 to 2 carbon atoms. In compounds having the structure of formula VIII, R is an alkyl having 1 to 4 carbon atoms; and $R^{33}$, $R^{34}$, $R^{35}$, $R^{36}$, $R^{37}$, $R^{38}$, $R^{39}$ and $R^{40}$ are independently selected from hydrogen or alkyl having 1 to 2 carbon atoms.

Alkylpyrrolidines having the structure of Formula IX wherein R is an alkyl having 1 to 4 carbon atoms; and $R^3$, $R^4$, $R^6$, $R^7$, $R^9$ and $R^{10}$ are independently selected from hydrogen or methyl, are the preferred compounds of Formula II. Preferred compounds of Formula IX, include the compounds of Formula X wherein R and $R^3$ are $CH_3$, and each of $R^4$, $R^6$, $R^7$, $R^9$ and $R^{10}$ is hydrogen, that is 1,2-dimethylpyrrolidine, the compounds of Formula XI wherein R is $CH_3$, and each of $R^3$ to $R^{10}$ is hydrogen, that is 1-methylpyrrolidine, and the compounds of Formula XII wherein R is $C^4H_9$, and each of $R^3$ to $R^{10}$ is hydrogen, that is 1-butylpyrrolidine. When the Lewis base is an alkylpiperidine of Formula VI, it is preferred that the alkylpiperidine has the structure of Formula XIII wherein R is methyl or ethyl, and each of $R^{11}$, $R^{12}$, $R^{14}$, $R^{16}$, $R^{18}$, $R^{19}$ and $R^{20}$ are hydrogen or methyl. Preferred alkylpiperidines of Formula XIII, include 1,2,2,6,6-pentamethylpiperidine (Formula XIV wherein each of R, $R^{11}$, $R^{12}$, $R^{19}$ and $R^{20}$ is methyl, and each of $R^{14}$, $R^{16}$ and $R^{18}$ is hydrogen), and 1-methylpiperidine and 1-ethylpiperidine (Formulae XV and XVI, respectively).

(IX)

(X)

(XI)

(XII)

(XIII)

(XIV)

(XV)

(XVI)

The preferred compounds among those of Formula im are the alkylmorpholines 4-methylmorpholine having the Formula XVII and 4-ethylmorpholine having the Formula XVIII. Among the alkylpiperazines of Formula VIII, 1,4-dimethylpiperazine having the Formula XIX is preferably reacted to form a complex which is then used as a precursor compound for alumina film deposition via chemical vapor deposition method.

(XVII)

(XVIII)

(XIX)

Thus, suitable organic amines of Formulae II and III include 1,2-dimethylpyrrolidine, 1-methylpyrrolidine, 1-butylpyrrolidine, 1,2,2,6,6-pentamethylpiperidine, 1-methylpiperidine, 1-ethylpiperidine, 4-methylmorpholine, 4-ethylmorpholine and 1,4-dimethylpiperazine.

As depicted in the following Reaction Scheme 1, the aluminum compound of Formula I, which is useful for alumina chemical vapor deposition, can be prepared by reacting a trialkylaluminum (Al(R'R"R'")) compound with a Lewis base such as an alkyl pyrrolidine, alkylpiperidine, alkylmorpholine, alkylpiperazine and the like, at room temperature.

Al(R'R"R'")+nL→(R'R"R'")Al:L$_n$          Reaction Scheme 1

In the tri-substituted aluminum compounds in the above Reaction Scheme 1, R', R" and R'" are independently selected from alkyl, perfluoroalkyl or alkoxy each of which has 1 to 5 carbon atoms, or borate (BH$_4$); L is an organic Lewis base, and n is an integer of 1 or 2. It is preferred that R', R" and R'" are independently selected from methyl, ethyl, iso-propoxy or sec-butoxy. Preferably, the compounds of Formula I are prepared using as the Lewis base alkylpyrrolidines such as 1-butylpyrrolidine or 1-methylpyrrolidine, or alkylpiperidines such as 1-ethylpiperidine, which belongs to is preferable as the precursor compound for film deposition.

Therefore, the present invention will be more specifically explained centering around 1-butylpyrrolidine trimethylaluminum having the Formula XX, 1-methylpyrrolidine triethylaluminum having the Formula XXI, 1-ethylpiperidine trimethylaluminum and 1-ethylpiperidine triethylaluminum having the Formulae XXII and XXIII, respectively. These compounds can be used as a CVD precursor for alurnina film deposition, which is used in the manufacture of semiconductor devices.

(XX)

(XXI)

(XXII)

(XXIII)

The aluminum compounds of the Formulae XX to XXIII exhibit the following effects when they are used as a precursor for alumina film deposition. First, since the film deposition using known aluminum compounds is carried out at a high temperature, undesirable carbon contamination may occur in the deposited film. In contrast, the compounds of the present invention, a monomer prepared by combining the existing compound with a Lewis base ligand, may reduce the degree of contamination in the deposited film by somewhat decreasing the temperature during the deposition.

Second, the alkylaluminum compound conventionally used as a CVD precursor may cause explosive inflammation when it contacts with water or air. To the contrary, the compounds of the present invention have a highly reduced inflammability and may exclude the hazardous factors for fire and personal accidents resulting from handling such compounds.

Third, the compounds of the present invention have a vapor pressure sufficiently high for chemical vapor deposition and an excellent thermal stability. The compounds do not decompose upon storage and exist as liquid phase-precursors. Therefore, during film deposition by chemical vapor deposition methods using a bubbler for delivering the precursor, the compounds of the present invention make it easy to exactly control the delivery rate, which is directly related to process reproducibility. The present compounds also make it possible to use other manners of precursor delivery, such as direct liquid injection or liquid delivery systems in addition to the bubbler method. This is a further advantage of the present compounds since they provide a wide opportunity for developing various processes.

Additionally, the present inventor has developed precursor solutions which can be used more conveniently for depositing an alumina film in a liquid delivery system, such as for example, direct liquid injection or other liquid delivery systems. As the solvent for making the precursor solutions, heterocyclic amines may be used, preferably 1-methylpyrrolidine, 1-butylpyrrolidine, 1-methylpiperidine, 1-ethylpiperidine, 4-methylmorpholine, 4-ethylmorpholine, 1,4-dimethylpiperazine, and the like. The compounds of Formula I dissolved in said solvents can be used as highly effective precursors for depositing alumina films.

In general, in the chemical vapor deposition methods, an alumina film is deposited on a substrate, such as a silicon substrate, heated to a deposition temperature of from 150 to 550° C. using an organometallic compound of Formula I. During such deposition process, vaporized water, in the form of steam, is provided. The water steam, particularly from ultrapure water, oxidizes the precursor aluminum to aluminum oxide through oxidation-reduction reaction in a reactor, and simultaneously forms a film on the substrate. In such chemical vapor deposition processes, thermal energy or plasma is used as the excitation source of the processing gas or a bias is applied on the substrate.

The precursor solution of the present invention is more advantageous than existing precursor solutions in view of the broad selection range for developing new deposition process of alumina film.

The novel precursor solutions may be prepared by dissolving the compounds of Formula I in a purified solvent free from moisture, wherein this solvent may be a Lewis base such as heterocyclic amine, and the like. Since the compound should be prevented from deterioration caused by the contact with air, the whole reaction procedure must be proceeded under inert gas such as nitrogen or argon.

The compound of the present invention and process for preparing the precursor solution will be more specifically explained in the following examples.

EXAMPLE 1

Synthesis of 1-Methylpyrrolidine Trimethylaluminum

Colorless 1-methylpyrrolidine, 212 g (2.5 mol), was added dropwise to 144 g (2 mol) of trimethylaluminum at room temperature under nitrogen gas flow with stirring. After the addition of 1-methylpyrrolidine was completed, the resulting mixture was stirred for 6 hours at room temperature to complete the reaction. 1-Methylpyrrolidine trimethylaluminum was obtained after completion of the reaction and was dried under vacuum at about 45° C. to give 300 g of a colorless liquid. The dried colorless liquid was distilled under vacuum ($10^{-2}$ torr) at 600° C., during which a colorless distillate was condensed inside a vessel cooled with dry ice. This first colorless distillate was purified according to the same procedure at 60° C. to give 267 g of the colorless and highly purified 1-methylpyrrolidine trimethylaluminum.

The chemical reaction shown in Reaction Scheme 2 is the preparation of 1-methylpyrrolidine trimethylaluminum, and the product was analyzed by proton ("$^1$H") nuclear magnetic resonance. The $^1$H nuclear magnetic resonance ("NMR") data and physicochemical properties of the highly purified 1-methylpyrrolidine trimethylaluminum are shown in the following Table 1.

Reaction Scheme 2

EXAMPLE 2

Synthesis of 1-Butylpyrrolidine Trimethylaluminum

The procedure of Example 1 was repeated, except that 292 g (2.3 mol) of 1-butylpyrrolidine was added dropwise to 144 g (2 mol) of trimethylaluminum under nitrogen gas flow with stirring. The resulting mixture was stirred for 6 hours at room temperature and then dried under vacuum at 50° C. to give a colorless liquid compound. Then, the dried colorless liquid compound was distilled under vacuum at 80° C. to give 330 g of the colorless liquid 1-butylpyrrolidine trimethylalurninum having high purity.

The chemical reaction shown in Reaction Scheme 3 is the preparation of 1-butylpyrrolidine trimethylaluminum, and the product was analyzed by $^1$H NMR. The $^1$H NMR data and physicochernical properties of the highly purified 1-butylpyrrolidine trimethylaluminum are shown in the following Table 1.

Reaction Scheme 3

EXAMPLE 3

Synthesis of 1-Methylniperidine Trimethylaluminum

The procedure of Example 1 was repeated, except that 218 g (2.2 mol) of 1-methylpiperidine was added dropwise to 144 g (2 mol) of trimethylaluminum under nitrogen gas flow with stirring. The resulting mixture was stirred for 6 hours at room temperature, dried under. vacuum at 60° C., and then distilled under vacuum at 95° C. to give 298 g of the colorless liquid 1-methylpiperidine trimethylaluminum having high purity.

The chemical reaction shown in Reaction Scheme 4 is the preparation of 1-methylpiperidine trimethylaluminum, and the product was analyzed by $^1$H NMR. The $^1$H NMR data and physicochemical properties of the highly purified 1-methylpiperidine trimethylaluminum are shown in the following Table 1.

Reaction Scheme 4

EXAMPLE 4

Synthesis of 1-Ethylpitieridine Trimethylaluminum

The procedure of Example 1 was repeated, except that 249 g (2.2 mol) of 1-ethylpiperidine was added dropwise to 144 g (2 mol) of trimethylaluminum under nitrogen gas flow with stirring. The resulting mixture was stirred for 6 hours at room temperature, dried under vacuum at 70° C., and then distilled under vacuum at 120° C. to give 315 g of the colorless liquid 1-ethylpiperidine trimethylaluminum having high purity.

The chemical reaction shown in Reaction Scheme 5 is the preparation of 1-ethylpiperidine trimethylaluminum, and the product was analyzed by $^1$H NMR. The $^1$H NMR data and physicochemical properties of the highly purified 1-ethylpiperidine trimethylaluminum are shown in the following Table 1.

Reaction Scheme 5

EXAMPLE 5

Synthesis of 1,4-Dimethylpiperazine Trimethylaluminum

The procedure according to Example 1 was repeated, except that 251 g (2.2 mol) of 1,4-dimethylpiperazine was added dropwise to 144 g (2.2 mol) of trimethylaluminum under nitrogen gas flow with stirring. The resulting mixture was stirred for 6 hours at room temperature, the mixture was separated, and then dried under vacuum to give 301 g of the solid 1,4-dimethylpiperazine trimethylaluminum.

The chemical reaction shown in Reaction Scheme 6 is the preparation of 1,4-dimethylpiperazine trimethylaluminum, and the product was analyzed by $^1$H NMR. The $^1$H NMR data and physicochemical properties of the highly purified 1,4-dimethylpiperazine trimethylaluminum are shown in the following Table 1.

Reaction Scheme 6

EXAMPLE 6

Synthesis of 4-Ethylmorpholine Trimethylaluminum

The procedure according to Example 1, 253 g (2.2 mol) of 4-ethylmorpholine was added dropwise to 144 g (2 mol) of trimethylaluminum under nitrogen gas flow with stirring. The resulting mixture was stirred for 6 hours at room temperature for reaction completion, and then the mixture was dried under vacuum at 65° C. and distilled under vacuum at 90° C. to give 329 g of the colorless 4-ethylmorpholine trimethylaluminum having high purity.

The chemical reaction shown in Reaction Scheme 7 is the preparation of 4-ethylmorpholine trimethylaluminum, and the product was analyzed by $^1$H NMR. The $^1$H NMR data and physicochemical properties of the highly purified 4-ethylmorpholine trimethylaluminum are shown in the following Table 1.

Reaction Scheme 7

EXAMPLE 7

Synthesis of 1-Methylpyrrolidine Triethylaluminum

Colorless 1-methylpyrrolidine, 195 g (2.3 mol), was added dropwise to 228 g (2 mol) of triethylaluminum at room temperature under nitrogen gas flow with stirring. After the addition of 1-methylpyrrolidine was completed, the resulting mixture was stirred for about 6 hours at room temperature to complete the reaction. 1-Methylpyrrolidine triethylaluminum was obtained after completion of the reaction, and was dried under vacuum at about 45° C. to give a colorless liquid. The dried colorless liquid compound was distilled under vacuum ($10^{-2}$ torr) at 70° C., during which a colorless distillate was condensed inside a vessel cooled with dry ice. This first colorless distillate was purified according to the same procedure at 70° C. to give 354 g of the colorless liquid 1-methylpyrrolidine triethylaluminum having high purity.

The chemical reaction shown in Reaction Scheme 8 is the preparation of 1-methylpyrrolidine triethylaluminum, and the product was analyzed by $^1$H NMR. The $^1$H NMR data and physicochemical properties of the highly purified 1-methylpyrrolidine triethylaluminum are shown in the following Table 1.

Reaction Scheme 8

EXAMPLE 8

Synthesis of 1-Butylpyrrolidine Triethylaluminum

The procedure of Example 7 was repeated except that 280 g (2.2 mol) of 1-butylpyrrolidine was added dropwise to 228 g (2 mol) of triethylaluminum under nitrogen gas flow with stirring. The resulting mixture was stirred for 6 hours at room temperature, dried under vacuum at 60° C. and then distilled under vacuum at 85° C. to give 420 g of the colorless liquid 1-butylpyrrolidine triethylaluminum having high purity.

The chemical reaction shown in Reaction Scheme 9 is the preparation of 1-butylpyrrolidine triethylaluminum, and the product was analyzed by $^1$H NMR. The $^1$H NMR data and physicocherical properties of the highly purified 1-butylpyrrolidine triethylaluminum are shown in the following Table 1.

Reaction Scheme 9

EXAMPLE 9

Synthesis of 1-Methylpiperidine Triethylaluminum

The procedure of Example 7 was repeated, except that 218 g (2.2 mol) of 1-methylpiperidine was added dropwise to 228 g (2mol) of triethylaluminum under nitrogen gas flow with stirring. The resulting mixture was stirred for 6 hours at room temperature, dried under vacuum at 60° C. and then distilled under vacuum at 75° C. to give 345 g of the colorless liquid 1-methylpiperidine triethylaluminum having high purity.

The chemical reaction shown in Reaction Scheme 10 is the preparation of 1-methylpiperidine triethylaluminum, and the product was analyzed by $^1$H NMR. The $^1$H NMR data and physicochemical properties of the highly purified 1-methylpiperidine triethylaluminum are shown in the following Table 1.

Reaction Scheme 10

EXAMPLE 10

Synthesis of 1-Ethylpiperidine Triethylaluminum

The procedure of Example 7 was repeated, except that 249 g (2.2 mol) of 1-ethylpiperidine was added dropwise to 228 g (2 mol) of triethylaluminum under nitrogen gas flow with stirring. The resulting mixture was stirred for 6 hours at room temperature, dried under vacuum at 65° C. and then distilled under vacuum at 80° C. to give 400 g of the colorless liquid 1-ethylpiperidine triethylaluminum having high purity.

The chemical reaction shown in Reaction Scheme 11 is the preparation of 1-ethylpiperidine triethylaluminum, and the product was analyzed by $^1$H NMR. The $^1$H NMR data and physicochemical properties of the highly purified 1-ethylpiperidine triethylaluminum are shown in the following Table 1.

Reaction Scheme 11

EXAMPLE 11

Synthesis of 1,4-Dimethylpiperazine Triethylaluminum

The procedure of Example 7 was repeated, except that 251 g (2.2 mol) of 1,4-dimethylpiperazine was added dropwise to 228 g (2 mol) of triethylaluminum under nitrogen gas flow with stirring. The resulting mixture was stirred for 6 hours at room temperature, dried under vacuum at 65° C. and then distilled under vacuum at 115° C. to give 365 g of the colorless liquid 1,4-dimethylpiperazine triethylaluminum having high purity.

The chemical reaction shown in Reaction Scheme 12 is the preparation of 1,4-dimethylpiperazine triethylaluminum, and the product was analyzed by $^1$H NMR. The $^1$H NMR data and physicochemical properties of the highly purified 1,4-dimethylpiperazine triethylaluminum are shown in the following Table 1.

Reaction Scheme 12

EXAMPLE 12

Synthesis of 4-Ethylmorpholine Triethylaluminum

The procedure of Example 7 was repeated, except that 253 g (2.2 mol) of 4-ethylmorpholine was added dropwise to 228 g (2 mol) of triethylaluminum under nitrogen gas flow with stirring. The resulting mixture was stirred for 6 hours at room temperature, dried under vacuum at 65° C. and then distilled under vacuum at 115° C. to give 412 g of the colorless liquid 4-ethylmorpholine triethylaluminum having high purity.

The chemical reaction shown in Reaction Scheme 13 is the preparation of 4-ethylmorpholine triethylaluminum, and the product was analyzed by $^1$H NMR. The $^1$H NMR data and physicochemical properties of the highly purified 4-ethylmorpholine triethylaluminum are shown in the following Table 1.

Reaction Scheme 13

TABLE 1

| Example | Compound | Phase at 20° C. | Color | $^1$H NMR in ppm ($C_6D_6$) |
|---|---|---|---|---|
| 1 | 1-Methylpyrrolidine trimethylaluminum | Solid Liquid at 30° C. | Colorless | −0.50(s, 9H), 1.28(t, 4H), 1.91(s, 3H), 2.30(s, br, 4H) |
| 2 | 1-Butylpyrrolidine trimethylaluminum | Liquid | Colorless | −0.50(s, 9H), 0.69(t, 3H), 0.89(m, 2H), 1.28(m, 6H), 2.07(br, 4H), 2.30(m, 2H), 2.91(br, 2H) |
| 3 | 1-Methylpiperidine trimethylaluminum | Liquid | Colorless | −0.45(s, 9H), 0.80(m, 4H), 1.08(m, 2H), 2.41(m, 4H), 2.69(t, 3H) |
| 4 | 1-Ethylpiperidine trimethylaluminum | Liquid | Colorless | −0.43(s, 9H), 0.84(m, 6H), 1.01(t, 3H), 2.38(m, 4H), 2.68(m, 2H) |
| 5 | 1,4-Dimethylpiperazine trimethylaluminum | Solid | Colorless | −0.50(s, 9H), 1.71(s, 6H), 2.4(br, 2H) |
| 6 | 4-Ethylmorpholine trimethylaluminum | Solid Liquid at 40° C. | Colorless | −0.5(s, 9H), 0.67(t, 3H), 1.96(q, 2H), 2.08(m, 4H), 3.45(m, 4H) |

TABLE 1-continued

| Example | Compound | Phase at 20° C. | Color | $^1$H NMR in ppm ($C_6D_6$) |
|---|---|---|---|---|
| 7 | 1-Methylpyrrolidine triethylaluminum | Liquid | Colorless | 0.08(q, 6H), 1.17(br, 4H), 1.38(t, 9H), 1.81(s, 3H), 1.94(m, 2H), 2.72(m, 2H) |
| 8 | 1-Butylpyrrolidine triethylaluminum | Liquid | Colorless | 0.11(q, 6H), 0.69(t, 3H), 0.88(m, 2H), 1.08(m, 2H), 1.30(m, 4H), 1.52(t, 9H), 2.07(m, 4H), 2.31(m, 2H), 2.87(m, 2H) |
| 9 | 1-Methylpiperidine triethylaluminum | Liquid | Colorless | 0.14(q, 6H), 0.83(t, 4H), 1.43(t, 9H), 1.75(s, 3H), 2.30(m, 4H), 2.71(m, 2H) |
| 10 | 1-Ethylpiperidine triethylaluminum | Liquid | Colorless | 0.15(q, 6H), 0.81(t, 6H), 1.0(m, 3H), 1.48(t, 9H), 2.3(m, 4H), 2.65(m, 2H) |
| 11 | 1,4-Dimethylpiperazine triethylaluminum | Liquid | Colorless | 0.05(m, 6H), 1.40(t, 9H), 1.85(s, 6H), 2.60(m, 8H) |
| 12 | 4-Ethylmorpholine triethylaluminum | Liquid | Colorless | 0.11(q, 6H), 0.69(t, 3H), 1.35(t, 9H), 1.96(m, 6H), 3.42(br, 4H) |

In order to confirm the solubility of the compounds obtained in Examples 1 to 12, the solutions of the following Examples 13 and 14 were prepared.

EXAMPLE 13

1-Ethylpiperidine Trimethylaluminum in 1-Ethylpiperidine

A colorless solution was obtained by adding 10 g of purified 1-ethylpiperidine to 90 g of the liquid compound 1-ethylpiperidine trimethylaluminum prepared according to Example 4.

EXAMPLE 14

1-Ethylpiperidine Triethylaluminum in 1-Ethylpiperidine

A colorless solution was obtained by adding 10 g of purified 1-ethylpiperidine to 90 g of the liquid compound 1-ethylpiperidine triethylaluminum prepared according to Example 10.

EXAMPLE 15

Another aspect of the present invention resides in the formation of aluminum oxide film using the compounds exemplified above while ultrapure water steam is provided. The ultrapure water steam oxidized the precursor aluminum to aluminum oxide through oxidation-reduction reaction in a reactor, and simultaneously makes a film on the substrate.

The experiments are carried out as below, and the results are represented in the following Tables 2 to 4.

The following experiments for vapor deposition of alumina film were carried out using solutions containing 1-butylpyrrolidine trimethylaluminum of Example 2, 1-ethylpiperidine triethylaluminum of Example 10, and 1-ethylpiperidine triethyl-aluminum of Example 14 which were each dissolved in 1-ethylpiperidine.

Experiment A

1-Butylpyrrolidine trimethylaluminum prepared according to Example 2 was introduced into a stainless steel bubbler, and was then melted by heating, at 65° C. The precursor compound was bubbled using argon or nitrogen as having a flow rate of 100 sccm (standard cubic centimeters per minute or cm$^3$/minute) as a delivery gas.

The precursor compound and ultrapure distilled water were contained in separate bubblers and were bubbled and vaporized. The vaporized precursor and water were introduced into a reactor in which a substrate to be film-deposited was located, while the stainless steel delivery conduit for the precursor was heated to 80° C. and that for water steam was heated to 100° C.

Figure 1:
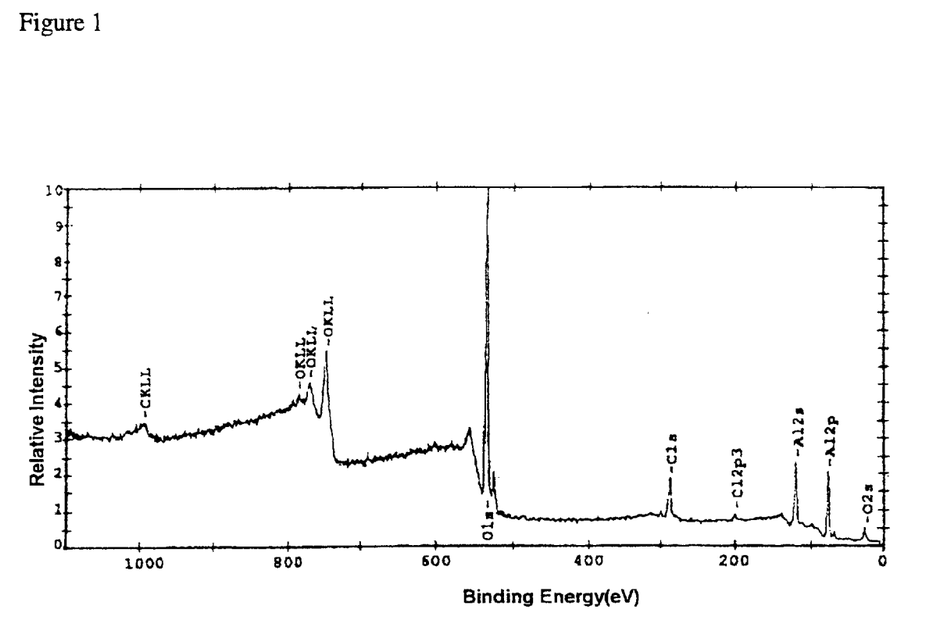
FIG. 1 is ESCA spectrum showing the composition and components of alumina film deposited on silicon substrate.

The reactor wall was heated to 80° C. to prevent the introduced precursor compound from condensing thereon. The high functional alumina film was vapor deposited on a silicon substrate at 350° C. on which SiO$_2$ of 2000 Å was already deposited. Components of the deposited film were analyzed by ESCA (Electron Spectroscopy for Chemical Analysis) to confirm that alumina film was actually deposited (see, FIG. 1). Conditions for vapor deposition and analysis data are represented in the following Table 2.

TABLE 2

| Precursor | Conditions for vapor deposition | | Film | |
|---|---|---|---|---|
| 1-Butylpyrrolidine trimethylaluminum | Delivery gas | Nitrogen or Argon | Deposition rate | 100–500 Å/min |
| | Reaction gas | Water steam | Dielectric constant (ε) | About 9.5 |
| | Bubbler temperature | 65° C. | Adhesive strength | Good for SiO$_2$ |
| | Reactor/Delivery conduit | 80° C. | Degree of Reflection | Good |
| | Substrate temperature | 350° C. | | |
| | Flow rate | 100 sccm | | |
| | Reactor Pressure | 100 mtorr~6 torr | | |

Experiment B

Alumina film deposition was carried out using 1-ethylpiperidine triethylaluminum compound prepared in Example 10. The conditions for vapor deposition and reactors were identical with those of Experiment A. The alumina film was deposited on a silicon substrate heated to 400° C. Composition and components of the deposited film were analyzed by ESCA, and the results are represented in the following Table 3.

TABLE 3

| Precursor | Conditions for vapor deposition | | Film | |
|---|---|---|---|---|
| 1-Ethylpiperidine triethylaluminum | Delivery gas | Nitrogen or Argon | Deposition rate | 100–500 Å/min |
| | Reaction gas | Water steam | Dielectric constant (ε) | About 9.5 |
| | Bubbler temperature | 65° C. | Adhesive strength | Good for $SiO_2$ |
| | Reactor/ Delivery conduit | 80° C. | Degree of Reflection | Good |
| | Substrate temperature | 400° C. | | |
| | Flow rate | 100 sccm | | |
| | Reactor pressure | 100 mtorr~6 torr | | |

Experiment C

Alumina film deposition was carried out using the precursor solution prepared in Example 14. Here, the same silicon substrate as Experiment A was used as the substrate; a tube having an inner diameter of 5 cm and a length of 30 cm, one side of which was closed and the other side was connected with a vacuum pump ($10^{-2}$ torr), was used; the precursor solution and ultrapure distilled water were introduced into each of 5 ml volume glass vessels, which were then located at the closed end of the reactor; several thin silicone plates were introduced into the center of glass tube; the precursor solution was heated to 85° C. and the substrate was heated to 300° C. using separate heat waves, during which the alumina film was deposited under controlling the exhaust pressure to $10^{-2}$ torr by vacuum pump. Deposition of alumina film was confirmed by ESCA (see, Table 4). As a result, it was identified that the solution according to the present invention can be suitably used for delivery system of liquid precursor such as direct liquid injection or liquid delivery system.

TABLE 4

| Precursor | Conditions for vapor deposition | | Film | |
|---|---|---|---|---|
| Solution of 1-ethylpiperidine triethylaluminum dissolved in 1-ethylpiperidine | Reaction gas | Water steam | Dielectric constant (ε) | About 9.5 |
| | Vapor temperature | 85° C. | Adhesive strength | Good for $SiO_2$ |
| | Substrate temperature | 300° C. | Rate of vapor deposition | 200–600 Å/min |
| | Reactor pressure | 1 torr~$10^{-1}$ torr | | |

As can be seen from Experiments A to C, the present invention provides some outstanding advantages, for example, the compound of the present invention may vaporize at 850 C or less; the substrate may be film-deposited at a broad temperature range from 250 to 450° C.; deposition rate, dielectric constant, adhesive strength, and degree of reflection of the alumina film on silicon substrate are comparatively excellent to the known compounds; and direct liquid injection or liquid delivery system can be used for the deposition.

Further, although the alumina film was deposited through the reaction of precursor compound with the vaporized water steam in the above experiments a to c, the precursor compound alone, without the water steam, can also be used for depositing an alumina film.

What is claimed is:

1. An organometallic complex useful for depositing a highly pure alumina film on a substrate by chemical vapor deposition, having the Formula I:

$$R'R''R'''Al:L_n \quad (I)$$

wherein R', R" and R'" are independently selected from alkyl, perfluoroalkyl or alkoxy each of which has 1 to 5 carbon atoms, or borate ($BH_4$); L is one or more organic Lewis bases capable of providing an unshared electron pair to the aluminum metal center selected from thiophene, thiopyran and organic amines of the Formula II:

(II)

wherein R is an alkyl having 1 to 4 carbon atoms; $R^1$ and $R^2$ are independently selected from hydrogen or alkyl having 1 to 2 carbon atoms; m is an integer of 2 to 8; and n is an integer of 1 or 2.

2. The organometallic complex of claim 1 wherein R', R" and R'" are independently selected from methyl, ethhyl, iso-proproxy or sec-butoxy.

3. The organometallic complex of claim 1 wherein the organic amine is selected from alkylaziridine, alkylazetidine, alkylpyrrolidine, alkylpiperidine, alkylhexamethyleneimine, or alkylheptamethyleneimine.

4. The organometallic complex of claim 3 wherein the organic amine is selected from 1,2-dimethylpyrrolidine, 1-methylpyrrolidine, 1-butylpyrrolidine, 1,2,2,6,6-pentamethylpiperidine, 1-methylpiperidine, or 1-ethylpiperidine.

5. The organometallic complex of claim 4 wherein the organic amine is selected from 1-butylpyrrolidine, 1-methylpyrrolidine, or 1-ethylpiperidine.

6. The composition of claim 5 wherein the one or more heterocyclic amine solvents are selected from 1-methylpyrrolidine, 1-butylpyrrolidine, 1-methylpiperidine, or 1-ethylpiperidine.

7. A vapor deposition precursor composition comprising. the organometallic complex of claim 1 and one or more heterocyclic amine solvents.

8. A process for alumina film formation including the step of vapor depositing an alumina film on a substrate, wherein the source of aluminum in the alumina film is a vapor deposition precursor comprising an organometallic compound of the Formula:

(I)

wherein R', R" and R'" are independently selected from alkyl, perfluoroalkyl or alkoxy each of which has 1 to 5 carbon atoms, or borate ($BH_4$); L is one or more organic Lewis bases capable of providing an unshared electron pair to the aluminum metal center selected from thiophene, thiopyran and compounds having the structure of Formulae II or III:

(II)

(III)

wherein R is an alkyl having 1 to 4 carbon atoms; $R^1$, $R^2$, $R^{21}$, $R^{22}$, $R^{23}$ and $R^{24}$ are independently selected from hydrogen or alkyl having 1 to 2 carbon atoms; X is oxygen or nitrogen having alkyl group; k and l are integers of 1 to 3; m is an integer of 2 to 8; and n is an integer of 1 or 2.

9. The process of claim 8 wherein the organometallic compound is vaporized by thermal energy, plasma or a bias applied on the substrate.

10. A process for preparing an organometallic compound of the Formula:

(I)

wherein R', R" and R'" are independently selected from alkyl, perfluoroalkyl or alkoxy each of which has 1 to 5 carbon atoms, or borate ($BH_4$); L is one or more organic Lewis bases capable of providing an unshared electron pair to the aluminum metal center selected from thiophene, thiopyran and compounds having the structure of Formula II:

(II)

wherein R is an alkyl having 1 to 4 carbon atoms; $R^1$ and $R^2$ are independently selected from hydrogen or alkyl having 1 to 2 carbon atoms; m is an integer of 2 to 8; and n is an integer of 1 or 2; including the step of combining in the absence of a solvent the organic Lewis base and a tri-substituted aluminum compound of the formula R'R"R'"Al, wherein R', R" and R'" are as defined above.

* * * * *